United States Patent
Butty et al.

(10) Patent No.: US 7,771,420 B2
(45) Date of Patent: Aug. 10, 2010

(54) SALINE-ENHANCED CATHETER FOR RADIOFREQUENCY TUMOR ABLATION

(75) Inventors: Jean-François Butty, Chexbres (CH);
Fernando Burdio, Saragossa (ES);
Antonio Laborda, Saragossa (ES)

(73) Assignee: Medelec-Minimeca S.A., Puidoux (CH)

( * ) Notice: Subject to any disclaimer, the term of this patent is extended or adjusted under 35 U.S.C. 154(b) by 459 days.

(21) Appl. No.: 10/591,150

(22) PCT Filed: Mar. 3, 2005

(86) PCT No.: PCT/IB2005/000564

§ 371 (c)(1),
(2), (4) Date: Aug. 30, 2006

(87) PCT Pub. No.: WO2005/089663

PCT Pub. Date: Sep. 29, 2005

(65) Prior Publication Data

US 2007/0185483 A1 Aug. 9, 2007

(30) Foreign Application Priority Data

Mar. 5, 2004 (EP) .................................. 04005356

(51) Int. Cl.
*A61B 18/14* (2006.01)
(52) U.S. Cl. ...................................................... 606/41
(58) Field of Classification Search .................. 606/15, 606/32–50; 600/374; 604/114
See application file for complete search history.

(56) References Cited

U.S. PATENT DOCUMENTS

| | | | |
|---|---|---|---|
| 5,938,659 A * | 8/1999 | Tu et al. ........................ 606/41 |
| 6,208,881 B1 * | 3/2001 | Champeau ................... 600/374 |
| 6,312,428 B1 * | 11/2001 | Eggers et al. .................. 606/41 |
| 6,537,248 B2 * | 3/2003 | Mulier et al. ................ 604/114 |
| 6,579,288 B1 | 6/2003 | Swanson et al. |
| 2001/0025176 A1 * | 9/2001 | Ellsberry et al. .............. 606/41 |
| 2002/0035361 A1 * | 3/2002 | Houser et al. .................. 606/15 |
| 2002/0107512 A1 | 8/2002 | Edwards |

FOREIGN PATENT DOCUMENTS

WO    WO 97/25917 A    7/1997

OTHER PUBLICATIONS

Gus J. Livaditis, DDS, Comparison of monopolar and bipolar electrosurgical modes for restorative dentistry: A review of the literature, Oct. 2001, The Journal of Prosthetic Dentistry, vol. 86 No. 4, 393-394.*

* cited by examiner

*Primary Examiner*—Michael Peffley
*Assistant Examiner*—Ronald Hupczey, Jr.
(74) *Attorney, Agent, or Firm*—Clifford W. Browning; Krieg DeVault LLP

(57) ABSTRACT

Catheter for the radiofrequency ablation of tissue, comprising at least one pair of bipolar electrodes adapted to function in bipolar mode, each bipolar electrode comprising supply channels adapted for the perfusion of saline solution around the electrodes, the catheter further comprising at least two end electrodes arranged towards opposed ends of the catheter, on either side of the pair of bipolar electrodes, said end electrodes adapted to function in monopolar mode.

8 Claims, 2 Drawing Sheets

SALINE-ENHANCED CATHETER FOR RADIOFREQUENCY TUMOR ABLATION

Figure 1:
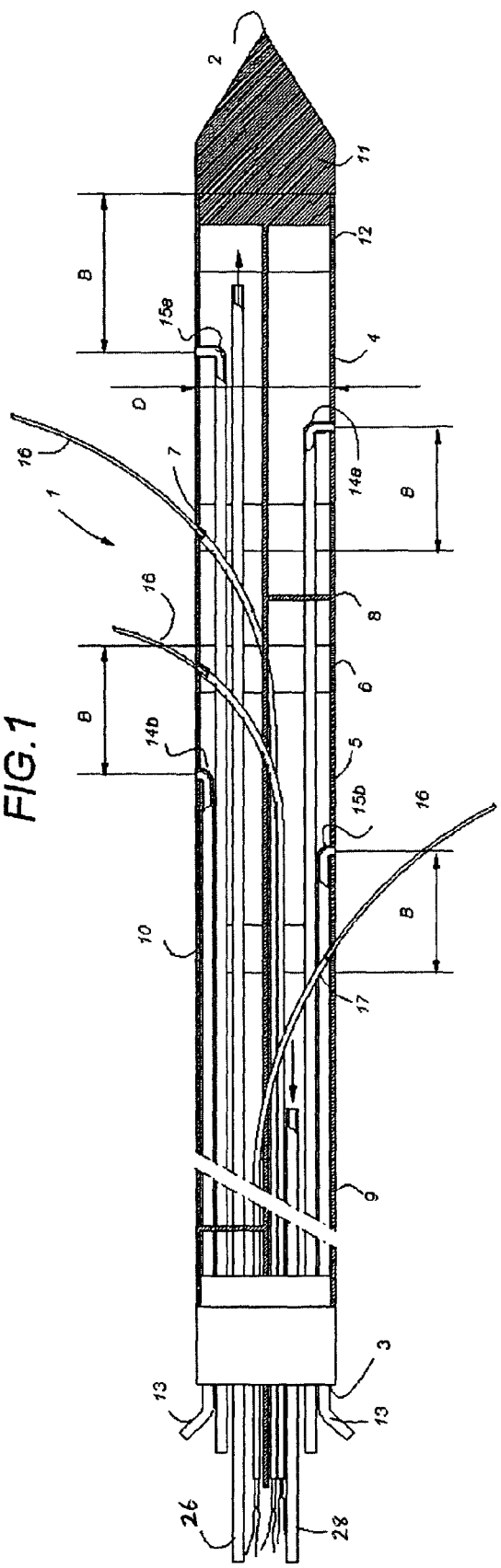

This application claims the benefit of PCT Patent Application Serial No. PCT/IB2005/000564, filed Mar. 3, 2005, which is now International Publication Number WO 2005/089663, published Sep. 29, 2005, which claims priority to European Patent Application No. EP04005356.3, filed Mar. 5, 2004.

The present invention relates to a device and method for thermal treatment of tissue, in particular for destroying tumors.

Thermal damage of undesired cells for tumor ablation by application of a high frequency electromagnetic field with a needle electrode is well known. The use of alternating current at frequencies greater than 10 kHz thermally excites the tissue molecules without causing pain or muscular contractions. At frequencies exceeding 900 MHz, heat dissipation is hard to control in view of the greater capacitive effects at these high frequencies. The working range of radiofrequency (RF) systems thus lies within the range of 10 kHz to 900 mHz.

Heating tissues to more than 50° C. leads to the breakdown of proteins and cellular membranes, which results in cellular death. The use of RF interstitial thermoablation to destroy tumors is dependent on the physician's ability to insert the needle-electrode into the tumor under ultrasound or computed tomographic guidance. Recently, there has been marked interest in image-guided RF tumor ablation as a minimally invasive thermal therapy, especially for focal metastasic and primary liver tumors, given the significant morbidity and mortality of standard surgical resection and the large number of patients that cannot tolerate such radical surgery.

In the most commonly used- monopolar electrode configurations, current flows from an electrosurgical probe in the form of a small active electrode through the tissues to a grounding electrode usually placed on the patient's thigh or back. In these conventional RF ablation devices, the current delivered to the tissue adjacent to the active electrode is proportional to $1/r^2$ from the electrode center, and the developed heat from translational molecular motion (ohmic or resistive heating) occurs in a very narrow rim around the electrode (proportional to $1/r^4$). The heat generated immediately adjacent to the electrode propagates through the tissue by thermal conduction. This implies a rapid rise of temperature to greater than 100° C. at the tissue-electrode interface, which causes desiccation and coagulum formation. Desiccated cellular tissues adhere to the electrode and form an electrically insulating coating resulting in a rapid and significant increase of impedance around the electrode with a subsequent power "roll-off". This effect precludes further RF energy conduction beyond the desiccated tissue and halts further tissue coagulation. Furthermore, blood flowing within the vessels acts as a heat sink and substantially limits the necrotizing effect of RF treatment in the adjacent tissue. Existing technology is limited in that only 3.5 to 4 cm diameter (about 33 cm³ of tissue volume) may be ablated in a single cycle. Therefore, to treat tumors larger than 2.5 cm in diameter, including at least 1 cm margin of healthy tissue rim, multiple overlapping ablations are required to encompass the tumor and the surrounding healthy tissue rim. Conventional methods are thus tedious and need to be performed with great precision.

One way to partly solve the problem of the monopolar mode that arises from the disadvantageous electric field distribution is to use the bipolar mode where the probes are both active and placed close to each other in the liver. However, only a slight increased lesion size can be obtained because of the above-mentioned phenomenon of increased impedance around the electrodes. Thus the lesions may never become confluent if the electrodes are separated more than 2-3 cm.

Another potential strategy to increase the efficacy of RF ablation is to infuse NaCI solutions into the tissue through an active electrode. Two reasons have been provided to explain the improved tissue heating and increased RF-induced coagulation with simultaneous saline infusion: (a) that NaCI alters electrical conductivity of the tissue to permit greater RF energy deposition, or (b) that the infusion of fluid during RF application improves the thermal conduction within the tissues by more rapidly and effectively convecting heat over a larger tissue volume avoiding the desiccation of the tissue around the electrodes at the same time. It has however been observed that monopolar saline-enhanced electrodes form irregularly shaped areas of coagulation with limited control of lesion size. With this method as in any monopolar method the current has to flow from a small active electrode with a small surface and high impedance, through the body to a much larger electrode often referred to as a "return electrode" placed on the patient's thigh or back. During the infusion of saline solution, the active electrode may be connected to the return electrode with a very large number of possible electric field lines, whereby RF energy can be dissipated at various undetermined distances from the active electrode. This could be an explanation for the lack of predictability of the lesions achieved with this method. Furthermore, with the conventional application of a saline-enhanced electrode in a monopolar way a dangerous reflux of heated saline solution through the puncture and extended to the biliary system have been observed, leading to some severe complications.

Considering the aforegoing, an object of this invention is to provide a device for thermal ablation of tissue enabling good control, predictability and regularity of the lesion shape. Moreover, operation and performance of the device should be highly reliable.

It is an advantage to provide a device for thermal ablation of tissue that is capable of treating a large volume of tissue in a single cycle.

It is an advantage to provide a device for thermal ablation of tissue that does not require a very high degree of precision, thereby facilitating operations, improving the quality of treatment, and reducing the risk of error and the implications of insufficiently precise manipulations.

Objects of this invention have been achieved by providing a device for thermal ablation of tissue according to claim 1, and a method of thermal ablation of tissue according to claim 10.

Disclosed herein is a catheter for the radiofrequency ablation of tissue, the catheter comprising at least one pair of electrodes adapted to function in bipolar mode, each electrode of the pair comprising supply channels adapted for the perfusion of saline solution around the electrodes, the catheter further comprising at least two end electrodes arranged towards opposed ends of the catheter on either side of the pair of bipolar electrodes, said end electrodes adapted to function in monopolar mode. A third monopolar electrode may advantageously be positioned between the pair of bipolar electrodes.

One of the functions of the monopolar electrodes is to seal the puncture performed by the catheter to better contain and control the perfusion of saline solution around the bipolar electrodes.

As each of the bipolar electrodes has its own saline solution supply channels, these may be independently supplied with saline solution, thus enabling a precise and predictable control of the lesion shape, in conjunction with the sealing of tissue around the catheter extremities and between the bipolar electrodes. The bipolar electrode configuration in the saline solution perfusion enables a better control and focus of the radiofrequency energy between the electrodes and is less sensitive than monopolar configurations to an uneven diffusion of saline solution, since the saline solution further away from the two electrodes will not dissipate RF energy as much as the solution close the electrodes. Furthermore in the bipolar mode the electric field gradient does not drop as sharply as in the monopolar mode and also stays fairly constant in the region between the probes. This advantage also becomes apparent when comparing the temperature distributions of the alternating monopolar mode and the bipolar modes.

Trials using two probes both perfused with independent pumps with a solution of NaCl show that it is possible to perform homogeneous and significant heating in the area of the tissue between the two probes regardless of the distance between them, on condition that the influence of blood cooling is limited. Thus predictable ellipsoids of coagulation necrosis in a large range of sizes can be generated with the device according to the present invention.

Advantageously, a device for the thermal ablation of tissue according to this invention enables the creation of a relatively large lesion with a regular shape, while eliminating overheating at the tissue-electrode interface and producing an approximately uniform temperature throughout the volume of tissue being treated. This overcomes the complications related to conventional devices and treatment methods.

The outlets of the saline solution supply channel in the bipolar electrodes are arranged at a small distance from respective extremities of the bipolar electrodes, the distance being sufficient to avoid obstruction by the coagulation effected by the monopolar electrodes.

The size of the lesion to be created will depend on the length of the catheter in the present invention, which can be easily adapted by providing longer or shorter bipolar electrodes and to some extent by adapting the length of the dielectric and of the central monopolar electrode separating the bipolar electrodes.

Thermal ablation of tissue with a device according to this invention may be performed according to the following procedure. The catheter is inserted into the patient's tissue and guided to the tumor or volume of tissue to be destroyed, with the assistance of an ultrasound or computer tomographic guidance apparatus, as performed in conventional treatments. Once in place, the monopolar electrodes are energized with radiofrequency electrical current, without a saline solution, to seal the punctured tissue around the monopolar electrodes. Subsequently, saline solution is pumped through the bipolar electrode supply channels into the tissue surrounding the electrodes, and the bipolar electrodes are supplied with radiofrequency alternating current to perform the thermal ablation of tissue. Voltages may be registered using an oscilloscope or similar equipment connected to the bipolar electrodes, and thermocouples mounted in the catheter connected to a temperature acquisition unit may be used to monitor the temperature at various positions along the catheter.

The thermocouples may advantageously be slidably mounted in the catheter and insertable a certain depth in the tissue surrounding the catheter in order to better measure the temperature in the tissue during treatment, and thus control of the amount of energy supplied and the duration of the operation.

Figure 2:
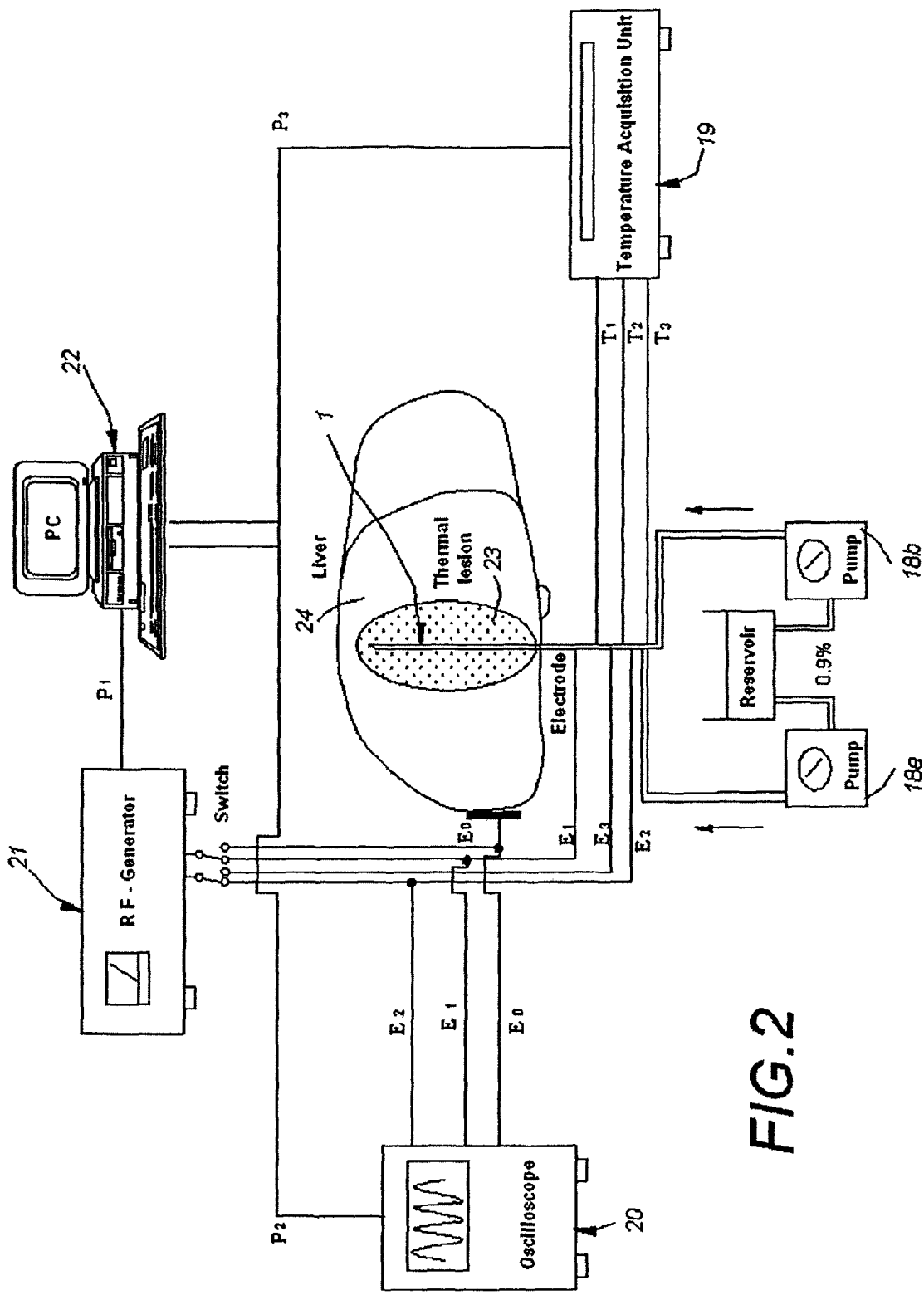

Further advantages and aspects of the invention will be apparent from the claims and following description of an embodiment of the invention and the appended drawings, in which FIG. 1 is a cross-sectional view illustrating an embodiment of a catheter according to this invention;

FIG. 2 is a simplified schema illustrating a system for thermal ablation of tissue connected to a device with catheter according to this invention.

Referring to the figures, a device 1 for thermal ablation of tissue, in the form of a catheter, with a long tubular shape extending from a pointed piercing or insertion tip 2 to a rear end 3 is shown. The diameter D of the catheter is preferably less than 3 mm in order to reduce the size of the puncture and adverse effects related thereto. The overall length of the catheter according to this invention will depend on the volume of the lesion to be created, whereby the length of the catheter is selected to be approximately equivalent to the size of the desired lesion. In the case of a tumor of say 6 cm in diameter, the selected length of the active part of the catheter will for example lie in the range of 7 to 9 cm.

The catheter comprises a pair of electrodes 4, 5 adapted to function in a bipolar manner (hereinafter "bipolar electrodes"), in the form of tubular metal elements arranged in a juxtaposed manner on a common axis and separated electrically by one or more dielectric elements 6, 7 from each other and with respect to a central electrode 8 adapted to function in a monopolar mode (hereinafter "central monopolar electrode"). Monopolar electrodes are also provided at extremities of the catheter, a rear monopolar electrode 9 separated from one of the bipolar electrodes 5 by an insulating element 10 and a front monopolar electrode 11 separated from the bipolar electrode 4 by an insulating element 12. The front monopolar electrode 11 may be shaped so as to form the pointed piercing tip of the catheter.

The catheter further comprises a plurality of liquid supply channels for perfusion of saline solution into the tissue surrounding the catheter. The supply channels are connected to outlets, for example in form of holes, feeding out of the periphery of the bipolar electrodes. Preferably, each bipolar electrode 4, 5 is provided with a supply channel with an outlet 14a, 14b, close to the center of the catheter, but arranged at a distance B sufficiently far from the central monopolar electrode 8 to avoid being obstructed by the coagulated tissue formed by the monopolar electrode during the initial phase of the operation. Each bipolar electrode also comprises preferably supply channel outlets 15a, 15b proximate outer ends of the bipolar electrodes, these outlets also preferably positioned at a distance B from respective monopolar end electrodes 9, 11 sufficient to avoid being obstructed by the coagulation around the outer monopolar electrodes. It is possible, within the scope of the invention, to provide further saline solution supply channels positioned and having outlets along the electrodes. One or more outlets may also be provided around the periphery of the catheter for each of the supply channels. In the configuration illustrated in FIG. 1, the central and outer supply channel outlets are preferably oriented in opposed directions in order to ensure a homogeneous distribution of saline solution around the catheter.

The central and outer electrodes are advantageously supplied with independent supply systems, in particular independent pumps 18a, 18b, in order to enable the perfusion of saline solutions of different salt concentrations around the ends of the catheter in relation to around the center of the catheter. It is thus possible to supply the ends of the catheter with a saline solution (typically sodium chloride solution) with a higher concentration than the saline solution supplied through the central outlets 14a, 14b, so as to improve electrical current flow through parts of the tissue that are distant from the catheter, thereby improving control of the lesion 23 shape and volume. Positioning of the outlets 15b, 14b and 14a, 15a towards the ends of each bipolar electrode 4, 5 improves electrical current distribution due to the preferential dissipation of the RF current near the ends of the electrodes.

The catheter may advantageously also comprise a plurality of thermocouples 16 at positions along the catheter in order to control the temperature during operation, not only the overall temperature but also the temperature distribution along the catheter. The thermocouples may be connected to a temperature acquisition unit 19 for monitoring during operation. The thermocouples are advantageously slidably mounted in conduits 17 in the catheter, and may be inserted a certain depth into surrounding tissue during operation in order to measure the temperature in the tissue being treated. This allows for a better control of RF power to be applied, as well as the duration of thermal treatment.

Other monitoring apparatus such as voltage sensors 20 connected to the electrodes, the pump flow, and the RF generator 21 may be interconnected to a control unit 22, for example such as a personal computer for monitoring and controlling parameters during operation.

The operation steps of the device according to this invention may be performed according to the following protocol. In the initial steps, a catheter of the appropriate length is selected, which should be at least 1 cm longer than the unhealthy tissue to be destroyed, for example a tumor, in order to encompass the tumor safely with the lesion 23. The catheter is guided with the assistance of an imaging system, such as an ultrasound or computer tomographic guidance system as known in the art, into the patient's tissue 24. A grounding pad or return electrode with a large surface is positioned on the patient's skin in an appropriate position as is known in the art.

Power is then supplied to the monopolar electrodes for a time sufficient to perform the coagulation and sealing of tissue around the monopolar electrodes, for example a power of 60 W for 20 seconds.

After the sealing operation, power to the monopolar electrodes is switched off and power is supplied to the bipolar electrodes and saline solution is pumped with the separate pumps independently to the central, respectively outer outlets of the supply channels in the bipolar electrodes 4, 5. Preferably, the required volume of saline solution or a portion thereof is pumped into the lesion prior to application of power to the bipolar electrodes. For example, 100 ml of saline solution with for example a concentration of 3% in salt for the central outlets, and 20% for the peripheral or outer outlets of each electrode is infused. RF ablation may then be started when a certain impedance is reached, for example 60Ω at a power output of 1 W. The power supply during RF ablation may be successively increased, for example 30 W the first minute, 60 W the second minute, and 90 W the third minute, whereby the RF ablation and perfusion of saline solution may be stopped either when the desired lesion is achieved with the assistance of the image guidance system, or based on empirical values obtained from prior experimentation. The thermocouples, inserted into the surrounding tissue after the catheter is inserted in its position of operation, allows the temperature of the tissue being treated to be monitored, thus providing information useful for control of the RF power and/or duration of treatment. Whereas the length of the thermal lesion will depend principally on the length of the catheter, the diameter of the generally ellipsoid-shaped lesion may be controlled by a combination of the concentration of the saline solution infused into the tissue and the power and duration of RF ablation. The thermocouples are retracted into the catheter after the end of treatment and prior to pulling the catheter out of the patient.

The catheter may advantageously be provided with a closed internal cooling circuit (not completely shown) connected to an inlet 26 and outlet 28 for a cooling fluid, that is preferably a physiological saline solution, to flow inside the catheter to cool the outer surface thereof. The cooling, in bipolar RF mode, participates in eliminating overheating at the tissue-electrode interface and in particular prevents coagulation and burning of tissue in contact with the catheter that may reduce conductivity and thus the effectiveness of the RF ablation treatment.

The invention claimed is:

1. Apparatus for radio frequency ablation of tissue comprising a catheter having a pointed tip for piercing insertion into said tissue, comprising at least one pair of bipolar electrodes functioning in bipolar mode and connected to a source of bipolar energy, each bipolar electrode comprising supply channels adapted for the perfusion of saline solution around the electrodes, the catheter further comprising at least two end electrodes arranged towards opposed ends of the catheter, on either side of the pair of bipolar electrodes, said end electrodes connected to a source of monopolar energy and functioning in monopolar mode, and at least two independently controlled pumps for supplying saline solution to separate supply channels of each bipolar electrode, further comprising a temperature acquisition unit connected to thermocouples of the catheter, the apparatus further comprising an RF generator, whereby the independently controlled pumps, RF generator, and temperature acquisition unit are connected to a computing unit, such as a PC, for monitoring and controlling operations.

2. Apparatus according to claim 1, wherein said supply channels comprise outlets (15*a*, 15*b*) arranged proximate said opposed ends of the catheter and outlets (14*a*, 14*b*) arranged proximate a center of the catheter, said outlets proximate the opposed ends being supplied with the saline solution independently of said outlets proximate the center.

3. Apparatus according to claim 1, wherein said catheter further comprises a central electrode (8) arranged between the bipolar electrodes (4, 5), the central electrode adapted to function in monopolar mode.

4. Apparatus according to claim 3, wherein outlets of said supply channels are arranged at a distance (B) from said central and end electrodes adapted to function in monopolar mode, that is sufficient to avoid being in a region of coagulated tissue formed around said electrodes adapted to function in monopolar mode.

5. Apparatus according to claim 1, further comprising one or more thermocouples (16), said thermocouples being retractably mounted in the catheter and actionable so as to be inserted into tissue surrounding the catheter.

6. Method of radiofrequency ablation of tissue, comprising the steps of:
providing a catheter having at least one pair of bipolar, electrodes with saline solution supply channels, and at least two monopolar electrodes arranged towards opposed ends of the catheter on either side of the pair of bipolar electrodes;
inserting the catheter into a central region of the volume of tissue to be ablated; supplying electrical power to the monopolar electrodes to coagulate tissue therearound and seal said tissue to said catheter around the puncture performed by the catheter;
perfusing saline solution into the tissue surrounding the bipolar electrodes and supplying electrical RF energy to the bipolar electrodes for thermal ablation.

7. Method according to claim 6, wherein the step of perfusing saline solution comprises supplying saline solution via supply channels (14*a*, 14*b*) arranged proximate the center of the catheter at a concentration lower than saline solution supplied to outlets (15*a*, 15*b*) arranged proximate opposed ends of the catheter.

8. Method according to claim 6, wherein prior to or during the step of operation of the bipolar electrodes, retractable thermocouples (16) mounted in the catheter are inserted at a certain depth into the surrounding tissue.

* * * * *